United States Patent [19]

Balzer et al.

[11] Patent Number: 4,695,412

[45] Date of Patent: Sep. 22, 1987

[54] PREPARATION OF ACYLOXYBENZENESULFONIC ACIDS AND THEIR ALKALI METAL AND ALKALINE EARTH METAL SALTS

[75] Inventors: Wolf-Dieter Balzer, Ludwigshafen; Hans-Heinrich Bechtolsheimer, Dittelsheim-Hessloch; Karl-Heinz Beyer, Frankenthal; Rolf Fikentscher, Ludwigshafen; Johannes Perner, Neustadt; Rudi Widder, Leimen; Helmut Wolf, Hassloch, all of Fed. Rep. of Germany

[73] Assignee: BASF Aktiengesellschaft, Rheinland-Pfalz, Fed. Rep. of Germany

[21] Appl. No.: 933,354

[22] Filed: Nov. 19, 1986

Related U.S. Application Data

[63] Continuation of Ser. No. 736,847, May 22, 1985, abandoned.

[30] Foreign Application Priority Data

May 26, 1984 [DE] Fed. Rep. of Germany ....... 3419795

[51] Int. Cl.$^4$ .......................................... C07C 143/52
[52] U.S. Cl. ................................................. 260/507 R
[58] Field of Search ........................ 260/512 R, 507 R

[56] References Cited

U.S. PATENT DOCUMENTS

| | | | |
|---|---|---|---|
| 2,487,586 | 8/1948 | Peterson | 260/512 R |
| 3,415,874 | 12/1968 | Lynch et al. | 260/512 R |
| 3,503,888 | 3/1970 | Miller et al. | |
| 3,686,127 | 8/1972 | Boldingh et al. | |
| 4,321,157 | 3/1982 | Harris et al. | |
| 4,412,934 | 11/1983 | Chung et al. | |

FOREIGN PATENT DOCUMENTS

| | | |
|---|---|---|
| 1618012 | 11/1970 | Fed. Rep. of Germany . |
| 864798 | 4/1961 | United Kingdom . |
| 1519351 | 7/1978 | United Kingdom . |

OTHER PUBLICATIONS

McOmle, Protective Groups in Org. Chem., 1973, pp. 171–177.
*Sulfonation and Related Reactions*, E. E. Gilbert (Allied Chemical Corp., Gen. Chemical Division, Morristown, N.J.) Interscience Publishers, 1965 (a division of John Wiley & Sons, N.Y.) pp. 1–31.
*Chemical Abstracts*, vol. 79, No. 1, Jul. 9, 1973, 4991c.
*Methoden der Organischen Chemie*, Houben Weyl, 4. Auflage, 1955, Georg Thieme Verlag, Stuttgart Band IX, Seiten 503–508.
Interscience Publishers, 1965, New York, E. E. Gilbert, "Sulfonation and Related Reactions", Seiten 7–20.

*Primary Examiner*—Alan Siegel
*Attorney, Agent, or Firm*—Oblon, Fisher, Spivak, McClelland, & Maier

[57] ABSTRACT

Acyloxybenzenesulfonic acids and their alkali metal and alkaline earth metal salts are prepared by a process comprising sulfonation of a phenyl ester in the presence or absence of a small amount of a complexing agent for the sulfonating agent $SO_3$ or chlorosulfonic acid, subsequent acylation and, if desired, neutralization to give the alkali metal or alkaline earth metal salt, and, if required, subjecting the latter to oxidative bleaching before drying.

9 Claims, No Drawings

PREPARATION OF ACYLOXYBENZENESULFONIC ACIDS AND THEIR ALKALI METAL AND ALKALINE EARTH METAL SALTS

This application is a continuation of application Ser. No. 736,847, filed on May 22, 1985, now abandoned.

The present invention relates to a process for the preparation of acyloxybenzenesulfonic acids and their alkali metal and alkaline earth metal salts by sulfonation of a phenyl ester in the presence or absence of a small amount of an agent which forms a complex with the sulfonating agent $SO_3$ or chlorosulfonic acid, followed by subsequent acylation and, if necessary, neutralization to give the alkali metal or alkaline earth metal salt, and if required oxidative bleaching of this salt prior to drying.

It is known that acyloxybenzenesulfonic acids, in the form of activated esters, are acylating agents for amines, mercaptans, hydrogen peroxide and other compounds containing active hydrogen. For some applications, such as the acylation of solids or of water-insoluble polymeric compounds, or the use as cold bleach activators in detergents, for example as described in European patent application No. 28,432, British Pat. No. 864,798, U.S. Pat. No. 4,412,934 or German Published application DAS No. 2,602,510, water-soluble acylating agents, such as the salts of acyloxybenzenesulfonic acids, eg. the conventional p-benzoyloxybenzenesulfonates or p-acetoxybenzenesulfonates, are advantageous.

Furthermore, the use of salts of acyloxybenzenesulfonic acids in toilet soaps is disclosed in, for example, U.S. Pat. No. 3,503,888, which describes a procedure for the preparation of acyloxybenzenesulfonic acids in which phenol is sulfonated with $SO_3$, and the resulting phenolsulfonic acid is esterified with a fatty acid chloride.

Because acyloxybenzenesulfonic acids are sensitive to hydrolysis, it is essential that they are prepared in the absence of water. For this reason, the conventional sulfonating agent sulfuric acid cannot be used. Sulfonation with $SO_3$ or chlorosulfonic acids, too, is as a rule not optimum. It usually takes place with formation of a mixture of o- and p-isomers, and a number of undesirable by-products, such as sulfones and their secondary products, are formed; transacylation gives rise to hydroxyketones and their secondary products, and ester cleavage also takes place. The by-products may interfere in subsequent working up to obtain a free-flowing salt, since they cause the product to cake readily.

The monograph by E. E. Gilbert, Sulfonation and Related Reactions, Interscience Publishers John Wiley and Sons, New York, 1965, Chapter 1, states, for example, that $SO_3$ and chlorosulfonic acid form complexes (generally 1:1 adducts) with a wide variety of organic compounds, such as amines, pyridine, ethers, amides, etc., and that these complexes are milder sulfonating reagents than $SO_3$ or chlorosulfonic acid itself. The reactivity of the sulfonating reagent can be influenced by means of this complex formation. As a rule, the sulfonation reactions with these complexes take place at higher temperatures than in the absence of a complexing agent and are frequently carried out in the presence of an inert solvent or an excess of complexing agent. A study of the stated reference shows that the reactivity of such a complex toward the substrate to be sulfonated cannot easily be predicted.

It is an object of the present invention to provide a process for the preparation of acyloxybenzenesulfonic acids and their alkali metal and alkaline earth metal salts which is easy to carry out on an industrial scale and gives the desired sulfonic acids in high purity and in good yields.

We have found that this object is achieved by a process for the preparation of acyloxybenzenesulfonic acids and their alkali metal and alkaline earth metal salts of the formula I

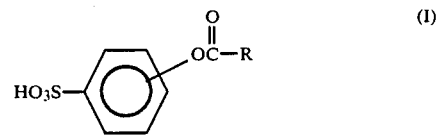

where R is straight-chain or branched saturated alkyl of 5 to 11 carbon atoms, by sulfonation of a phenyl ester, wherein a phenyl ester of the formula II

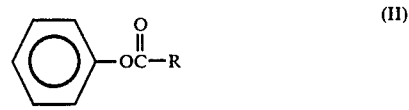

where R has the meanings given for formula I, in the presence or absence of from 0.2 to 30, preferably from 1 to 20, mole %, based on $SO_3$ or chlorosulfonic acid, of a complexing agent for $SO_3$ or chlorosulfonic acid, is sulfonated with $SO_3$ or chlorosulfonic acid at from 20° to 80° C., preferably from 25° to 55° C., the resulting reaction mixture is subsequently acylated with an acyl chloride of the formula Cl—COR, where R has the meanings stated for formula II, and, if required, the acyloxybenzenesulfonic acid obtained is then neutralized to give the alkali metal or alkaline earth metal salt, and, if required, the aqueous solution of the latter is subjected to oxidative bleaching before drying.

The starting compounds of the formula II are advantageously prepared by direct reaction of phenol with a carboxylic acid chloride of the formula Cl—COR or with a symmetric anhydride of the formula RCO—O—COR, where R has the meanings given for formula I, at from 40° to 60° C. in a conventional manner.

This esterification can advantageously also be carried out in the form of an azeotropic esterification of phenol with a carboxylic acid of the formula R—COOH, where R has the meanings given for formula I, expediently in an excess of from 5 to 10 mole %, and in the presence of an aromatic hydrocarbon, such as xylene or toluene, as an entraining agent for separating off the water formed, and of a strongly acidic esterification catalyst, such as p-toluenesulfonic acid, sulfuric acid, phosphorous acid, hypophosphorous acid or a mixture of these acids, the mixture subsequently being distilled.

The sulfonation, according to the invention, of the phenyl esters of the formula II is carried out directly with $SO_3$ or chlorosulfonic acid in the absence of a solvent at the above temperatures.

In a particularly preferred embodiment, the sulfonation is effected with the addition of a relatively small amount of an agent which forms a complex with the $SO_3$ or chloro-sulfonic acid, as described in, for example, the abovementioned monograph by Gilbert.

In the presence of these additives, the sulfonation leads to very pure products at relatively low temperatures. Surprisingly, the conventional 1:1 adducts of $SO_3$ or of chlorosulfonic acid react only very slowly, if at all, in the temperature range according to the invention. Moreover, a fairly large amount of complexing agent employed, eg. an amine, gives rise to additional expense in the working-up procedure if it is intended to obtain a very pure end product.

Specific examples of complex-forming compounds are dioxane, polyalkylene oxides, such as diethylene and dipropylene glycol, whose terminal groups are blocked by alkyl radicals of 1 to 18 carbon atoms, formamide, aliphatic carboxamides of 1 to 10 carbon atoms which are substituted at the amide nitrogen by 1 or 2 alkyl radicals of 1 to 4 carbon atoms, eg. dimethylformamide, diethylformamide or dibutylformamide, benzamides, 5-membered to 7-membered cyclic amides which are unsubstituted or substituted at the nitrogen by an alkyl radical of 1 to 4 carbon atoms, eg. N-methylpyrrolid-2-one, N-methylpiperid-2-one or -caprolactam, triazine derivatives, such as melamine, benzoguanamine or acetoguanamine, trialkylamines where alkyl is of 1 to 6 carbon atoms, $N,N-C_1-C_4$-dialkylcyclohexylamines, pyridine, triphenylphosphine, amidosulfonic acid, imidazole and boron trifluoride. If appropriate, mixtures of these complexing agents may also be used.

Among these, the N,N-disubstituted formamides where alkyl is of 1 to 4 carbon atoms, in particular dimethylformamide and 1,4-dioxane are particularly preferred.

In the novel process, the complex-forming compound is advantageously added to the liquid phenyl ester.

Examples of suitable alkyl radicals R of 5 to 11 carbon atoms are pentyl, heptyl, 2-ethylpentyl, octyl, branched octyl radicals and undecyl.

R is particularly preferably n-heptyl, n-octyl or 3,5,5-trimethylpentyl.

In the preparation, the pure acyl chlorides may advantageously be replaced with the industrially obtainable mixtures, which as a rule contain not less than 95% of a defined acyl chloride Cl—COR. In industrial terminology, 3,5,5-trimethylhexanoyl chloride is often referred to as isononanoyl chloride.

Otherwise, the reaction mixture formed preferentially contains the compound in which the radical —O—COR in formula I is in the p-position, together with some of the o-compound.

When the phenyl ester to be sulfonated is reacted with $SO_3$ or chlorosulfonic acid, it is advantageous to maintain a molar ratio of about 1:1 in order to avoid, for example, sulfone formation and disulfonation and further by-products. Deviations from the exact molar amount advantageously amount to no more than 5 mole % of excess sulfonating agent.

The hydrogen chloride formed when chlorosulfonic acid is used can be removed virtually completely and without difficulties by degassing, for example under reduced pressure of from 10 to 40 mbar.

The sulfonation reactions described here, including the esterification reactions, can be carried out batchwise or continuously.

In the procedure adopted in the continuous embodiment, for example, the reactants can be combined in a tube reactor or in a stirred kettle cascade.

In the crude acyloxybenzenesulfonic acid obtained, it is generally possible to detect products which have free phenolic hydroxyl groups and are formed by ester cleavage which takes place as a side reaction during sulfonation. Their amount can be determined potentiometrically, and reesterification can be effected by means of an equimolar amount of the carboxylic acid chloride of the formula Cl—COR, where R has the meanings given for formula I. This reaction is carried out at from 40° to 50° C. in the course of from 2 to 3 hours.

For practical reasons, and because the resulting acyloxybenzenesulfonic acids, being activated phenol esters, are very sensitive to hydrolysis and susceptible to decomposition, it is advantageous to convert the liquid acyloxybenzenesulfonic acids obtained into their alkali metal or alkaline earth metal salts, the sodium salt being particularly preferred. In an expedient and particularly advantageous neutralization procedure, the liquid acyloxybenzenesulfonic acid is combined with an aqueous solution of an alkali metal or alkaline earth metal hydroxide, carbonate or bicarbonate in water at from 0° to 60° C., preferably from 10° to 50° C., with thorough stirring, so that a pH of from 2.5 to 7.0, preferably from 3.0 to 5.5, is maintained, and, if required, the resulting salt is isolated in solid form from the aqueous solution in a conventional manner.

This special neutralization process in which acyloxybenzenesulfonic acids can be neutralized without significant hydrolysis forms the subject of the unpublished German patent application P No. 33 37 921.1. The specific procedure adopted is as follows: the liquid acyloxybenzenesulfonic acid and a 5-50% strength by weight aqueous solution of an alkali metal or alkaline earth metal hydroxide, carbonate or bicarbonate are run simultaneously into water at from 0° to 60° C., preferably from 10° to 50° C., while stirring, so that a pH of from 2.5 to 7.0, preferably from 3.0 to 5.5, is maintained.

This neutralization procedure can be carried out batchwise or continuously. In the continuous procedure, the components water, acyloxybenzenesulfonic acid and alkali are combined in a static or dynamic mixer.

Using this neutralization process, it is possible to prepare stable aqueous solutions of the acyloxybenzenesulfonates in concentrations of from 20 to 60% by weight. The pure salts can be isolated from these solutions in a conventional manner, for example by evaporation, drum-drying, spray-drying, freeze-drying or drying in a fluidized-bed dryer.

In a particularly preferred embodiment, this special neutralization procedure is carried out in the presence of from 1 to 2% by weight, based on the acyloxybenzenesulfonic acid, of a water-soluble phosphate, phosphite or tartrate or of a complexing agent for heavy metals or of a polymer of acrylic acid and/or maleic acid. As rule, the water-soluble sodium salts are used.

The aqueous solutions possess substantially less color, and have less tendency to become decolorized during further processing, if the neutralization is carried out in the presence of these substances. Specific examples are sodium dihydrogen phosphate, disodium tartrate, sodium hydrogen tartrate, sodium phosphite, hypophosphorous acid, nitrilotriacetic acid, ethylenediaminetetraacetic acid, diethylenetriaminepentaacetic acid, hydroxyethylethylenediaminetriacetic acid, nitrilotrimethylenephosphonic acid and polycarboxylic acids obtained from acrylic acid and/or maleic acid, and their sodium salts. The polyacrylic acids used have K values of from 15 to 120, while the acrylic acid/maleic acid copolymers possess K values of from 30 to 100, measured in each case on the completely neutralized Na salt in 1% strength by weight aqueous solution at 25° C.

It should be pointed out that the sulfonation of phenyl esters by the novel process gives rise to byproducts which, particularly when chlorosulfonic acid is used, condense to give colored compounds and also cause discoloration of the spray-dried product. These impurities can be lightened oxidatively by adding sodium perborate, hydrogen peroxide or sodium peroxodisulfate to the neutralized solution in an amount of from 0.05 to 2% by weight, based on the solids content of the aqueous solution, and heating the solution to 40°–80° C., preferably 45°–55° C., in the course of from 5 to 15, preferably from 8 to 11, hours. Thereafter, drying can be carried out.

EXAMPLES

The Examples below were carried out using compounds in which R was 3,5,5-trimethylpentyl, unless stated otherwise. Other acyl radicals exhibit entirely similar behavior. The content of acyloxybenzenesulfonic acid in the reaction mixture is advantageously determined after neutralization with aqueous sodium hydroxide solution and spray-drying, on the isolated sodium salts, by means of two-phase titration according to DIN/ISO 2271. Parts are by weight.

General Methods

A. Preparation of the Phenyl Esters as Starting Compounds of the Formula II 1. 94 parts of phenol were melted, and 176 parts of 3,5,5-trimethylhexanoyl chloride (isononanoyl chloride) were added at 45° C. in the course of from 1 to 2 hours, while stirring. Stirring was continued for 1 hour at 50° C.

2. 158 parts of isononanoic acid, 103 parts of phenol and 60 parts of toluene were heated at the boil with 1 part of p-toluenesulfonic acid and 0.3 part of hypophosphorous acid. 15 parts of water were separated off by azeotropic distillation at from 140° to 160° C., after which the toluene and the excess phenol were distilled off under 20 mbar at up to 140° C. The crude phenyl ester obtained was purified by distillation at from 140° to 160° C. and under reduced pressure of about 20 mbar. The yield was 187 parts (80%).

B. Sulfonation of the Phenyl Esters without Complexing Agents

Either 122 parts of chlorosulfonic acid or 84 parts of sulfur trioxide, according to the Table, were added to 234 parts of phenyl isononanoate at from 25° to 55° C. in the course of from 1 to 2 hours, stirring was continued for 1 hour at 50° C., and the hydrogen chloride was then removed under reduced pressure of from 10 to 20 mbar.

C. Sulfonation of the Phenyl Esters with Complexing Agents

The complexing agents shown in the Table were added to 234 parts of phenyl isononanoate. 122 parts of chlorosulfonic acid or 84 parts of sulfur trioxide were run into the cooled mixture in the course of from 1 to 2 hours at a rate such that the temperature did not exceed 55° C. Stirring was continued for 1 hour at 50° C., after which the hydrogen chloride was removed under reduced pressure of from 10 to 20 mbar.

D. Subsequent Acylation

The amount of phenolic OH groups present in the crude acyloxybenzenesulfonic acid was determined by titration with 1N aqueous sodium hydroxide solution using a Metrohm Titroprocessor (manufactured by Metrohm), and the said OH groups were then esterified with an equimolar amount of isononanoyl chloride in the course of 2 hours at 50° C. In the case of procedure B or C, from 4 to 20 parts of isononanoyl chloride were required for this purpose.

E. Neutralization and Oxidative Bleaching 100 parts of the crude acyloxybenzenesulfonic acid obtained were run into 100 parts of water, while stirring thoroughly. At the same time, 50% strength by weight aqueous sodium hydroxide solution was added dropwise so that the aqueous solution was brought to a pH of from 3.0 to 5.5 (monitored by means of a glass electrode). The temperature of the reaction mixture was kept below 50° C. by cooling. When the addition of the acyloxybenzenesulfonic acid was complete, the solution was brought to pH 5.5. For oxidative bleaching, 0.1 part of sodium perborate was added and the solution was then heated at 50° C. for 6 hours. The sodium salt was isolated from the aqueous solution by spray-drying.

F. Preparation of Sodium n-pentanoyl- and Undecanoyloxybenzenesulfonate 1. 188 parts of phenol were melted, and 269 parts of caproyl chloride (n-pentanecarbonyl chloride) were added at 45° C. in the course of from 1 to 2 hours. Stirring was continued for 1 hour at 50° C., after which 8 parts of dimethylformamide were added.

244 parts of chlorosulfonic acid were run in over 1–2 hours at a rate such that the temperature did not exceed 55° C.

Stirring was continued for 1 hour at 50° C., after which the remaining hydrogen chloride was removed under reduced pressure of from 10 to 20 mbar.

The crude sulfonic acid obtained was worked up as described in Examples D and E. Content: 81.1% of Na salt.

2. 141 parts of phenol, 328 parts of lauroyl chloride (undecanecarbonyl chloride), 8 parts of dimethylformamide and 183 parts of chlorosulfonic acid were reacted with one another, and the reaction mixture was worked up, these steps being carried out as described in Example F1. Content: 85.3% of active substance (Na salt).

TABLE

| | Examples according to process steps B to E | | | | | Content of Na salt[2] of the acyloxybenzene- |
|---|---|---|---|---|---|---|
| Example | ClSO$_3$H | SO$_3$ | Complexing agent | Parts | Mole %[1] | sulfonic acid |
| 1 | x | — | — | — | — | 75.7% |
| 2 | — | x | — | — | — | 74.3% |
| 3 | x | — | dimethylformamide | 2.34 | 3.0 | 85.0% |
| 4 | x | — | dimethylformamide | 4.68 | 6.1 | 84.1% |
| 5 | x | — | dimethylformamide | 9.36 | 12.3 | 87.6% |
| 6 | x | — | dimethylformamide | 14.04 | 18.3 | 86.4% |
| 7 | x | — | dioxane | 4.68 | 5.0 | 86.7% |
| 8 | x | — | dioxane | 14.04 | 15.2 | 86.5% |
| 9 | x | — | dioxane | 23.4 | 25.3 | 84.5% |
| 10 | x | — | urea | 4.68 | 7.4 | 84.3% |

TABLE-continued

Examples according to process steps B to E

| Example | ClSO₃H | SO₃ | Complexing agent | Parts | Mole %[1] | Content of Na salt[2] of the acyloxybenzene-sulfonic acid |
|---|---|---|---|---|---|---|
| 11 | x | — | tetramethylurea | 4.68 | 3.8 | 86.6% |
| 12 | x | — | tetramethylurea | 9.36 | 7.6 | 83.8% |
| 13 | x | — | imidazole | 4.68 | 6.6 | 83.1% |
| 14 | x | — | diisobutylformamide | 4.68 | 4.5 | 82.6% |
| 15 | x | — | melamine | 2.34 | 1.8 | 81.8% |
| 16 | x | — | benzoguanamine | 4.68 | 2.4 | 81.2% |
| 17 | x | — | N—methylpyrrolidone | 4.68 | 4.0 | 82.4% |
| 18 | x | — | N—methylpyrrolidone | 9.36 | 7.9 | 84.7% |
| 19 | x | — | dimethylcyclohexylamine | 9.36 | 7.0 | 83.0% |
| 20 | x | — | succinimide | 9.36 | 9.0 | 85.9% |
| 21 | x | — | phthalimide | 9.36 | 6.0 | 82.7% |
| 22 | x | — | triphenylphosphine | 9.36 | 3.4 | 84.5% |
| 23 | x | — | ethylene glycol dimethyl ether | 4.68 | 5.0 | |
| 24 | — | x | dimethylformamide | 11.17 | 14.6 | 80.9% |
| 25 | — | x | triethylamine | 9.36 | 8.8 | 80.7% |
| 26 | — | x | phthalimide | 9.36 | 6.0 | 78.7% |
| 27 | — | x | tetramethylurea | 9.36 | 7.6 | 79.5% |
| 28 | — | x | dimethylcyclohexylamine | 9.36 | 7.0 | 77.3% |
| 29 | — | x | N—methylpyrrolidone | 9.36 | 7.9 | 82.0% |
| 30 | x | — | dimethylformamide | 44 | 57 | 71.8% |
| 31 | x | — | dimethylformamide | 73 | 100 | 79.2% |
| 32 | — | x | dimethylformamide | 73 | 100 | — |
| 33 | x | — | urea | 60 | 100 | — |

[1]based on sulfonating agent
[2]two-phase titration according to DIN/ISO 2271

The values in the Table show that the addition of complexing agents, particularly where chlorosulfonic acid is used, results in a yield about 11% higher than that obtained without the addition of these complexing agents.

Examples 30 to 33 are comparative examples, about which the following may be stated: the use of dimethylformamide in an amount of 57 mole % leads to a substantially lower content of active substance (Example 30).

Regarding Example 31, reaction with an equimolar amount of dimethylformamide gave a content of active substance of 79.2%, the temperature having to be increased to 90° C. since no reaction took place at 55° C. The higher temperatures had the effect of imparting a pronounced dark coloration to the product, in spite of bleaching and additives.

Examples 32 and 33 gave inhomogeneous mixtures which did not react in the temperature range according to the invention, up to 80° C.

We claim:

1. A process for the preparation of alkali metal or alkaline earth metal salts of an acyloxybenzenesulfonic acid of the formula I

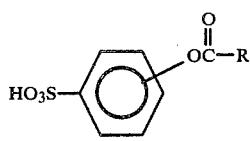
(I)

where R is straight-chain or branched saturated alkyl of 5 to 11 carbon atoms, by sulfonation of a phenyl ester, wherein a phenyl ester of the formula II

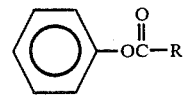
(II)

where R has the meanings given for formula I, in the presence of from 0.2 to 30 mole %, based on SO₃ or chlorosulfonic acid, of a complexing agent for SO₃ or chlorosulfonic acid, is sulfonated with SO₃ or chlorosulfonic acid at from 20° to 80° C., the molar ratio of phenyl ester to SO₃ or chlorosulfonic acid being about 1:1, the resulting acyloxybenzenesulfonic acid is subsequently acylated at 40°–50° C. with an acyl chloride of the formula Cl—COR, where R has the meanings stated for formula II, said acyl chloride being in an equimolar amount based on the free phenolic OH groups present, and the acyloxybenzenesulfonic acid obtained is then neutralized to give the alkali metal or alkaline earth metal salt, said neutralization being effected by combining the resulting liquid acyloxybenzenesulfonic acid of the formula I with an aqueous solution of an alkali metal or alkaline earth metal hydroxide, carbonate or bicarbonate in water at from 0° to 60° C., with thorough mixing, so that a pH of from 3.0 to 5.5 is maintained, and, if required, the aqueous solution of the latter is subjected to oxidative bleaching before drying.

2. A process as claimed in claim 1, wherein a phenyl ester of the formula II is sulfonated directly with SO₃ or chlorosulfonic acid at from 25° to 55° C.

3. A process as claimed in claim 1, wherein the sulfonation of a phenyl ester of the formula II is carried out in the presence of from 1 to 20 mole %, based on SO₃ or chlorosulfonic acid, of a complexing agent for SO₃ or chlorosulfonic acid, at from 25° to 55° C.

4. A process as claimed in claim 1, wherein the neutralization is carried out at from 10° to 40° C.

5. A process as claimed in claim 1, wherein the neutralization is carried out in the presence of from 1 to 2% by weight, based on the acyloxybenzenesulfonic acid, of a soluble phosphate, phosphite or tartrate, of a complexing agent for heavy metal salts or of a polymer obtained from acrylic acid and/or maleic acid.

6. A process as claimed in claim 1, wherein the neutralized solution is oxidatively lightened with from 0.05 to 2% by weight, based on the solids content, of sodium perborate, hydrogen peroxide or sodium peroxodisulfate, at from 40° to 80° C., in the course of from 5 to 15 hours.

7. A process as claimed in claim 1, wherein the complexing agent is selected from the group consisting of dimethylformamide, dioxane, urea, tetramethylurea, imidazole, diisobutylformamide, melamine, benzoguanamine, N-methylpyrrolidone, dimethylcyclohexylamine, succinimide, phthalimide, triphenylphosphine, ethylene glycol dimethyl ether and triethylamine.

8. A process as claimed in claim 7, wherein the complexing agent is dimethylformamide.

9. A process as claimed in claim 7, wherein the complexing agent is dioxane.

* * * * *